United States Patent

Ritter et al.

[11] Patent Number: 5,840,993
[45] Date of Patent: Nov. 24, 1998

[54] WATER-SOLUBLE COBALT CATALYSTS, PROCESS FOR THEIR PREPARATION AND THEIR USE AS HYDRO-FORMYLATION CATALYSTS IN A TWO-PHASE SYSTEM WITH POLYETHYLENE GLYCOL AS THE POLAR PHASE

[75] Inventors: Uwe Ritter; Norbert Winkhofer; Herbert Roesky, all of Göttingen, Germany

[73] Assignee: Hoechst AG, Frankfurt am Main, Germany

[21] Appl. No.: 981,261

[22] PCT Filed: Jun. 3, 1996

[86] PCT No.: PCT/EP96/02394

§ 371 Date: Feb. 26, 1998

§ 102(e) Date: Feb. 26, 1998

[87] PCT Pub. No.: WO97/00132

PCT Pub. Date: Jan. 3, 1997

[30] Foreign Application Priority Data

Jun. 16, 1995 [DE] Germany .......... 195 21 936.8

[51] Int. Cl.$^6$ .................................................. C07C 45/50
[52] U.S. Cl. .......... 568/545; 568/451; 568/909; 502/74; 502/232; 502/260; 502/158
[58] Field of Search ............. 502/74, 232, 158, 502/260; 568/451, 545, 909

[56] References Cited

U.S. PATENT DOCUMENTS 4,045,493  8/1977  Trevillyan .

OTHER PUBLICATIONS

Dietmar Seyferth et al, "Novel Silicon Compounds Containing The Nonacarbonyl Tricobaltcarbon Substituent", *Journal of Organometallic Chemistry*, 1979, pp. 227–247, XP002009593.

John Evans et al, "Generalised Cluster Anchoring to Oxide Supports", *J.C.S. Chem. Comm.*, 1980, pp. 852–853, XP002009594.

Maurice M. Kreevoy et al, "A General, High Yield Route to Novel Silicon–Functional Silymethylidynetricobalt Nonacarbonyl Cluster Complexes", *Journal of the American Chem. Soc.*, 1977, pp. 5209–5210, XP002009595.

*Primary Examiner*—Gary Geist
*Assistant Examiner*—Seeni Padmanabhan

[57] ABSTRACT

The invention relates to cobalt carbonyl catalysts of the formula (I)

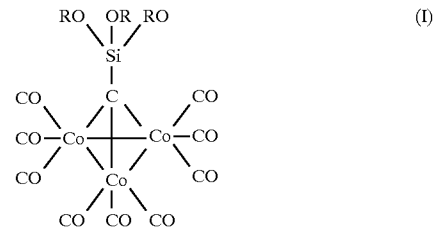

where R is $-CH(CH_2OCH_2CH_3)_2$ or $-C_2H_4(OCH_2CH_2)_n OY$, with n=1 to 12 and Y=H or $CH_3$, and also a process for their preparation and their use as hydroformylation catalysts.

19 Claims, No Drawings

WATER-SOLUBLE COBALT CATALYSTS, PROCESS FOR THEIR PREPARATION AND THEIR USE AS HYDRO-FORMYLATION CATALYSTS IN A TWO-PHASE SYSTEM WITH POLYETHYLENE GLYCOL AS THE POLAR PHASE

This is the U.S. National stage Application of PCT/EP96/02394 filed Jun. 3, 1996 now WO97/00132 published Jan. 3, 1997.

The invention relates to water-soluble cobalt catalysts, a process for their preparation and their use as hydroformylation catalysts in a two-phase system comprising polyethylene glycol as polar phase.

Water-soluble catalysts offer great industrial advantages owing to the ease of separating off the catalyst with at the same time high selectivity of the catalyst as a result of the homogeneous reaction procedure. The reduced primary energy consumption resulting from the ease of separating off the catalyst together with the simultaneous reduction in amounts of undesired by-products achieved as a result of the high selectivity is leading to an increasing interest in two-phase catalysts.

There is therefore a need for further compounds of this type to be made available.

This object is achieved by means of cobalt carbonyl catalysts of the formula (I)

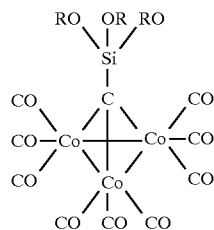

where R is —CH(CH$_2$OCH$_2$CH$_3$)$_2$ or —C$_2$H$_4$(OCH$_2$CH$_2$)$_n$OY, with n=1 to 12 and Y=H or CH$_3$.

The compounds of the invention are prepared by reacting compounds of the formula (II) with alcohols (ROH):

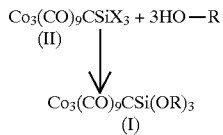

Here, X is OH or chlorine,

R is as defined above.

Compounds of the formula (II) are obtainable by the method of D. Seyferth, J. Organomet. Chem. 1979, 178, 227–247.

Compounds of the formula (I) display high conversion rates and chemoselectivities in the hydroformylation of olefins. Of particular interest is the reaction of olefins of the formula CH$_3$(CH$_2$)$_m$CH=CH$_2$ (m=2 to 9) in a two-phase system comprising polyethylene glycol as polar phase. It has here been found useful to work at temperatures of from 50° to 150° C., pressures of from 50 to 100 kPa and a concentration ratio of catalyst:substrate of from 1:20 to 1:1000.

EXAMPLE 1

0.574 g (1 mmol) of trichlorosilylmethylidynyl-tricobalt nonacarbonyl is taken up in 10 ml of polyethyleneglycol [lacuna] 400 and heated at 80° C. for 24 hours under a CO atmosphere. The sediment is subsequently filtered off. The CO content is 13.75 g/l (determined by atomic absorption spectroscopy). The compound is in the form of a solution in polyethylene glycol 400 and has an intense violet color. It is completely miscible with water and is virtually immiscible with nonpolar solvents (hexane, pentane, etc.).

The IR spectrum of the solution shows the following bands in the carbonyl region: 1887 cm$^{-1}$, 1979 cm$^{-1}$, 1995 cm$^{-1}$, 2029 cm$^{-1}$, 2060 cm$^{-1}$.

EXAMPLE 2

0.574 g (1 mmol) of trichlorosilylmethylidynyl-tricobalt nonacarbonyl is taken up in 10 ml of 1,3-diethoxy-2-propanol and heated to 60° C. for 24 hours under a CO atmosphere. The excess alcohol is subsequently distilled off in a high vacuum. The compound is obtained in the form of a violet high-viscosity solution. The IR spectrum of the compound in nujol shows the following bands in the carbonyl region:

2037 cm$^{-1}$, 2056 cm$^{-1}$. The $^1$H-NMR spectrum shows three groups of signals at: 1.03 ppm (CH$_3$,d,6H); 3.26 ppm (CH$_2$,q,4H); 3.42 ppm (CH$_2$,m,4H); 4.01 ppm (CH,m,1H) (measured in d$_6$-benzene). The $^{29}$Si-NMR spectrum shows a singlet at −53.8 ppm (measured in d$_8$-THF).

EXAMPLES 3 to 6

Use of the compound prepared under 1 for the hydroformylation of 1-hexene in polyethylene glycol 400:

The catalysis tests are carried out in a 100 ml laboratory autoclave. In a typical reaction, 2 ml of the polyethylene glycol solution which has been prepared by reaction of trichlorosilylmethylindynyl-tricobalt nonacarbonyl with polyethylene glycol 400 in the manner described (I) are initially charged and admixed with 2 ml of 1-hexene (16 mmol). The autoclave is then charged with 70 kPa of a mixture (1/1) of CO and H$_2$. The reaction mixture is heated at 120° C. for 18 hours while stirring. After the reaction, 4 ml of pentane are added to assist phase separation and the phases are separated. The upper nonpolar phase contains pentane and the reaction products which are determined gas-chromatographically by comparison with authentic samples or by GC-MS. Heptane serves as internal standard. The lower polyethylene glycol phase contains the catalyst and can be reused without pretreatment. The results are summarized in Table 1.

EXAMPLES 7 to 13

Catalysis tests using Co$_3$(CO)$_9$CSiX$_3$ (X=OH) (III) were carried out as comparative experiments using a method similar to Examples 5 to 8, under the conditions indicated in Table 1.

TABLE 1

| Example[a] | Temp. °C. | Pressure Kpa[b] | mg Co[c] | Yield %[d] | Time h | Selectivity n/iso[e] |
|---|---|---|---|---|---|---|
| 3 | 120 | 70 | 13.75 | 96.5 | 18 | 0.73 |
| 4 | 120 | 70 | 20.6 | 99.5 | 18 | 0.75 |
| 5 | 120 | 70 | 34 | 99.9 | 18 | 0.75 |
| 6[h] | 120 | 70 | 34 | 72.9 | 18 | 0.67 |
| 7 | 120 | 70 | 10.9 | 96.8 | 24 | 1.4 |
| 8 | 120 | 70 | 7.8 | 98.0 | 24 | 0.79 |
| 9 | 120 | 126 | 7.8 | 97.0 | 12 | 3.75 |
| 10 | 120 | 42 | 7.8 | 25.0 | 72 | 1.81 |
| 11 | 120 | 70 | 7.8 | 98.5 | 72 | 1.93 |

TABLE 1-continued

| Example[a] | Temp. °C. | Pressure Kpa[b] | mg Co[c] | Yield %[d] | Time h | Selectivity n/iso[e] |
|---|---|---|---|---|---|---|
| 12[f] | 120 | 70 | 11.6 | 98.9 | 24 | 3.2 |
| 13[g] | 120 | 70 | 10.2 | 99.8 | 24 | 2.96 |
| $CO_2(CO)_8$ | 120 | 70 | 22 | 95.6[i] | 18 | 0.58 |

[a]Examples 3 to 6 without solvent, Examples 7 to 13 using toluene as solvent
[b]initial pressure
[c]substrate: 2 ml of 1-hexene
[d]yields are based on the amount of 1-hexene consumed. The main products detected were 1-heptanal, 2-methylhexanal and 2-ethylpentanal. Hydrogenation of 1-hexene and of the aldehydes to give alcohols was not able to be observed under the reaction conditions indicated.
[e]n/iso: 1 heptanal/2-methylhexanal + 2 ethylpentanal
[f]addition of triphenylphosphine (molar ratio to the catalyst 1:1)
[g]addition of bis(diphenylphosphino)methane (molar ratio to the catalyst 1:1)
[h]reused catalyst after phaee separation
[i]chemoselectivity: 44% of aldehydes/56% of alcohols

We claim:

1. Cobalt carbonyl catalyst of the formula (I)

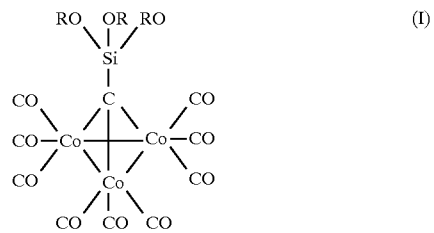

where R is $-CH(CH_2OCH_2CH_3)_2$ or $-C_2H_4(OCH_2CH_2)_n OY$, with n=1 to 12 and Y=H or $CH_3$.

2. A process for preparing a compound of formula (I) of claim 1, which comprises reacting a compound of formula (II)

$$Co_3(CO)_9CSiX_3 \quad (II)$$

with an alcohol of the formula ROH, where R is as defined in claim 1 and X is OH or Cl.

3. A solution comprising a compound of formula (I) of claim 1 dissolved in a polar liquid solvent for said compound.

4. A solution according to claim 3, wherein said polar liquid solvent is water, polyethylene glycol, or 1,3-diethoxy-2-propanol.

5. A reaction medium having a plurality of phases, comprising:
   in a first, polar phase, a compound of formula (I) of claim 1 dissolved in a polar liquid solvent for said compound, and
   in a second, nonpolar phase, an olefin.

6. A reaction medium as claimed in claim 5, wherein the catalyst for the reaction taking place in the reaction medium comprises a compound of formula I; wherein the olefin is a substrate for the reaction taking place in the reaction medium, and wherein the ratio of catalyst:substrate ranges from 1:20 to 1:1000.

7. A reaction medium according to claim 5, wherein said first phase is homogenous, and wherein said second phase further comprises a nonpolar solvent to assist in the separation of the two phases.

8. A reaction medium according to claim 7, wherein the nonpolar solvent is pentane or hexane.

9. A reaction medium according to claim 5, wherein a mixture comprising CO and $H_2$ is introduced into said medium as a means for conducting a hydroformylation of said olefin.

10. A reaction medium according to claim 5, wherein said olefin is a compound of the formula $CH_3(CH_2)_mCH=CH_2$, wherein m ranges from 2 to 9.

11. A reaction medium according to claim 5, wherein said olefin is subjected to a hydroformylation reaction, and wherein the hydroformylation products are obtained from said nonpolar phase of the reaction medium.

12. A process of hydroformylation, comprising the step of carrying out the hydroformylation in the presence of a compound of formula (I) of claim 1 as the catalyst for the hydroformylation.

13. A process according to claim 12, wherein the compound subjected to hydroformylation is an olefin.

14. A process according to claim 13, wherein said olefin is a compound of the formula $CH_3(CH_2)_mCH=CH_2$, wherein m ranges from 2 to 9.

15. A process according to claim 12, wherein said process is carried out at a temperature ranging from 50° to 150° C.

16. A process according to claim 12, wherein said process is carried out in a pressurized zone under a pressure ranging from 50 to 100 kPa.

17. A process according to claim 12, wherein the ratio of the compound of formula (I) to the substrate for the hydroformylation ranges from 1:20 to 1:1000.

18. A process according to claim 12, comprising:
   introducing into a reaction zone a compound of formula (I), a polar liquid solvent, an olefin, CO, and $H_2$;
   forming, within said reaction zone, a plurality of phases including a polar phase containing said compound of formula (I) dissolved in said polar liquid solvent, and a nonpolar phase containing at least one hydroformylation product; and
   separating said polar phase from said nonpolar phase.

19. A process according to claim 18, wherein a nonpolar solvent is added to said reaction zone to assist in the separation of the nonpolar phase from the polar phase, and wherein the polar phase is reused in a subsequent hydroformylation reaction.

* * * * *